(12) United States Patent
Torstensen et al.

(10) Patent No.: US 8,398,615 B2
(45) Date of Patent: Mar. 19, 2013

(54) PACKAGING FOR A MEDICAL ARTICLE AND A CATHETER IN SUCH A PACKAGING

(75) Inventors: Jan Torstensen, Virum (DK); Marlene Corydon, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 793 days.

(21) Appl. No.: 12/309,364

(22) PCT Filed: Jul. 10, 2007

(86) PCT No.: PCT/EP2007/057046
§ 371 (c)(1),
(2), (4) Date: Nov. 16, 2009

(87) PCT Pub. No.: WO2008/009590
PCT Pub. Date: Jan. 24, 2008

(65) Prior Publication Data
US 2010/0087801 A1    Apr. 8, 2010

Related U.S. Application Data

(60) Provisional application No. 60/831,467, filed on Jul. 18, 2006.

(30) Foreign Application Priority Data

Jul. 18, 2006   (DK) .................................. 2006 00992

(51) Int. Cl.
*A61M 1/00*    (2006.01)

(52) U.S. Cl. ......................................... 604/544; 206/438
(58) Field of Classification Search .................. 604/171, 604/263, 264, 317, 540–544; 206/438
See application file for complete search history.

(56) References Cited

U.S. PATENT DOCUMENTS

| 5,738,213 | A | 4/1998 | Whiting |
| 2003/0004496 | A1 | 1/2003 | Tanghoj |
| 2004/0158231 | A1 | 8/2004 | Tanghoj et al. |
| 2006/0025753 | A1 * | 2/2006 | Kubalak et al. ............... 604/544 |
| 2006/0142737 | A1 | 6/2006 | Tanghoj |

FOREIGN PATENT DOCUMENTS

| CN | 1717261 | 1/2006 |
| WO | WO99/67156 | 12/1999 |
| WO | WO 03/092779 | 11/2003 |
| WO | WO 2004/050155 | 6/2004 |

* cited by examiner

*Primary Examiner* — Melanie Hand
(74) *Attorney, Agent, or Firm* — Coloplast Corp., Coloplast A/S; Daniel G. Chaplik; Nicholas R. Baumann

(57) ABSTRACT

The invention provides a packaging for a medical article e.g. for a urinary catheter. The medical article is stored in a compartment and can be accessed by detaching a first element from a second element thereby forming an opening into the compartment. The first element comprises a suction cup or another fastening element by which the packaging is attachable to a surface. Due to the structure of the packaging, it can be supported in an orientation in which the opening is remote from the surface, and risk of contamination of the medical article can therefore be reduced during removal of the article from the packaging.

7 Claims, 4 Drawing Sheets

PACKAGING FOR A MEDICAL ARTICLE AND A CATHETER IN SUCH A PACKAGING

Figure 1:
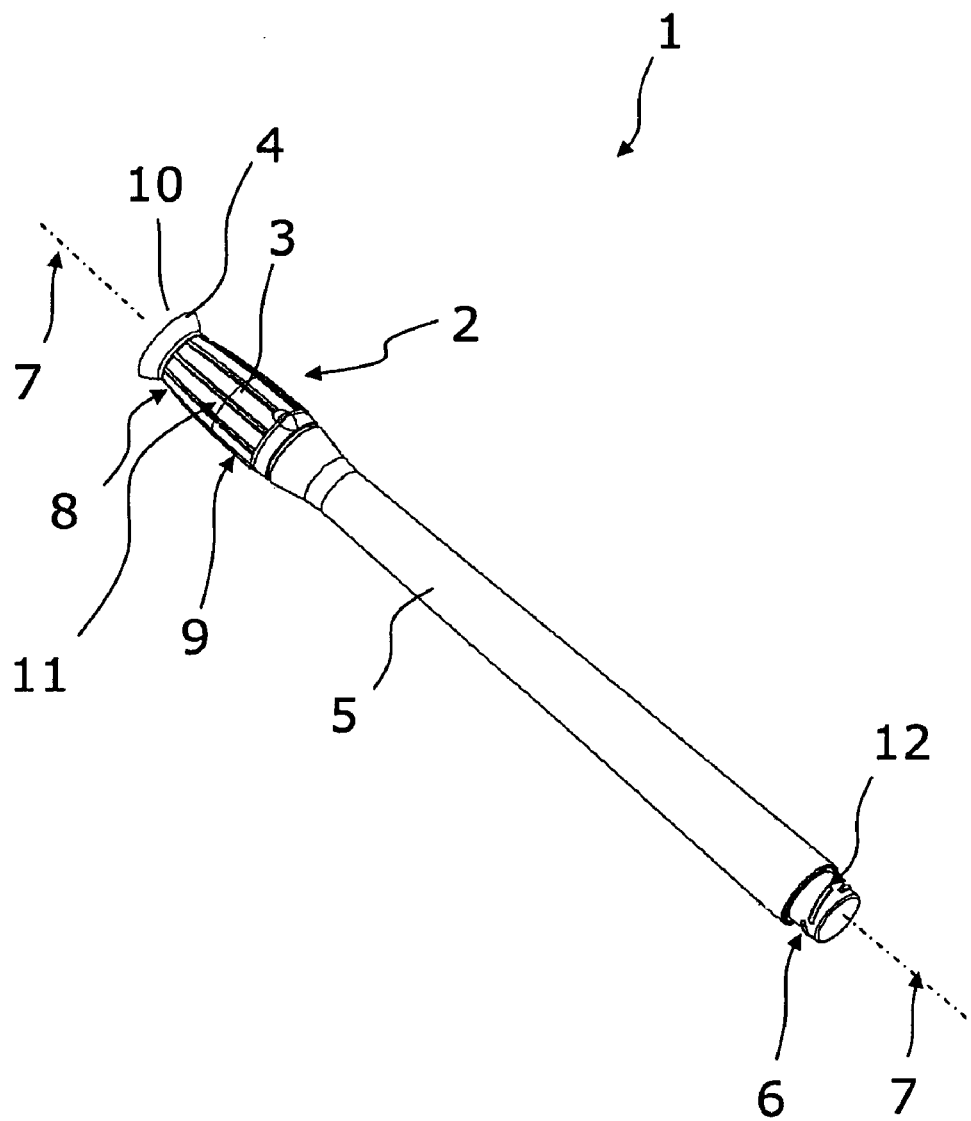

This is a national stage of PCT/EP07/057046 filed Jul. 10, 2007 and published in English, which has a priority of Denmark no. PA 2006 00992 filed Jul. 18, 2006, claiming benefit of US provisional application no. 60/831,467, filed Jul. 18, 2006, hereby incorporated by reference.

INTRODUCTION

The invention relates to a packaging with a compartment containing a medical article. The packaging comprises first and second detachably joined elements, wherein separation of the elements forms an opening into the compartment and thereby provides access to the medical article. The invention particularly relates to a packaging for a catheter, and in particular for a urinary catheter.

BACKGROUND OF THE INVENTION

Typically, medical articles are stored in a sterile condition. Most packaging for medical articles are designed mainly with focus on maintaining the sterility and protecting the article, e.g. from sun light, rough handling, or transportation.

In some packages, a certain opening procedure is implicit in the package design. As an example, it has become practise to pack medical items between two sheets of a foil material. When such packages are opened, the medical article is partly or completely exposed and can therefore be contaminated.

With respect to catheters, e.g. for urinary catheterisation, numerous attempts have been made to make opening easier, and to ensure a minimum exposure of the article in question. In particular, attempts have been made to avoid contamination of critical areas of the catheter such as the tip portion which is Inserted into the body during use. Accordingly, packages exist which facilitate use of a catheter without having completely to remove the catheter from the package. Sometimes, the package serves for manipulating the article without direct contact between the hands of the user and the catheter, and sometimes, the package includes a handling structure enabling non-contaminating removal and use of the article in question.

Even though existing packages may improve handling of medical articles by keeping the users hands away from critical areas, the risk of contamination still exist, e.g. due to the risk of coming into contact with surrounding objects during handling of the article.

Catheters for draining the bladder are used for intermittent as well as indwelling or permanent catheterisation. Typically, catheters are used by patients suffering from urinary retention, e.g. para- or tetraplegics who may have no control permitting voluntary urination. If the user suffers from reduced dexterity, removal of a catheter from a package may be further complicated. For supporting handling of medical articles, some packaging comprises suspension means, e.g. adhesives or through holes for suspending the packaging on a wall, e.g. of a restroom. In this case, the opening into the packaging becomes directly adjacent the wall, and the article may thus easily come in contact with the wall during removal of the article from the packaging.

DESCRIPTION OF THE INVENTION

It is an object of an embodiment of the invention to improve handling of medical articles and to reduce the risk of contaminating such articles during use. Accordingly, the invention, in a first aspect, provides a packaging of the kind mentioned in the introduction wherein the packaging comprises a base which is adapted to attach the packaging to a surface of an object in an orientation relative to the surface in which the opening is remote from the surface.

In a packaging in accordance with the invention, the medical article can be stored in a sterile state until use. At this time, the packaging is secured to a surface of an object, and the second element is removed. Since the packaging can be secured with the opening remote from the surface, the risk of hitting the surface, and thus the risk of contaminating the medical article, is reduced. In addition, the ability of securing the packaging to a surface makes handling easier since it is not necessary for the user to hold the packaging by the hands while removing the medical article.

In particular, the first and second elements may form the entire cavity, and the elements may be completely separate from the medical article thus rendering the article movable in the cavity relative to the first and second elements. Optionally, partly or completely removal of the medical article from the first and second elements is possible when the cavity has been opened by separation of the elements from each other.

The opening could e.g. be located a distance in the range of ⅕-½ times the longest length of the packaging or even longer away from the surface to which the packaging is attached. In one embodiment, the base is located in one axial end portion of the packaging and the opening is provided in an axially opposite end portion, i.e. furthest possible away from the base.

To support the packaging and to allow the packaging to extend away from the surface, at least a portion of the packaging between the base and the opening could be dimensionally stable, or at least have a rigidity enabling the packaging to protrude outwardly and/or upwardly from the base towards the opening. By "dimensionally stable" is meant that the part being dimensionally stable preserves its shape in any position and orientation, also if it is placed in different orientations on a surface.

By "attach" is meant that the article remains in contact with the surface for a period of time which is sufficient for removing the article from the packaging, and optionally sufficient for inserting the article into the packaging after use, e.g. a period of 30 seconds to 15 minutes. In this period of time, a force exceeding the force which is normally required to lift the packaging from the surface is necessary for releasing the packaging from the surface, and the packaging is capable of remaining on the surface in an orientation with the opening remote from the surface. The attaching strength depends on the shape of the article, and in particular on the location of the centre of gravity relative to the base. However, the packaging may be designed so that a force of 0.05-50 Newton in excess of the force which is required to remove the medical article from the packaging is required for lifting the packaging and thus releasing the packaging from the surface to which it is attached. In particular, the packaging may be designed so that it requires a relatively large force in one direction to separate the packaging from the surface to which it is attached, e.g. a large vertically directed force to lift the packaging from a horizontal surface. In this embodiment, the packaging may be designed so that it is relatively easy, i.e. requires less force, if it is lifted off from the surface in other directions, i.e. In directions being non-perpendicular to the surface to which it is attached. Such a characteristic may be obtained by using a suction cup for attaching the packaging to the surface.

In the following, the invention is described with reference to a catheter for urinary drainage. The article could, however, be a medical article of any suitable kind. Catheters for urinary drainage typically comprise an elongated body extending between a proximal insertable tip and an axially opposite distal end. In the insertable end, drainage eyes could be provided for draining urine from the bladder into an inner conduit, and in the distal end, the catheter may comprise a connector e.g. for attaching a collection bag or for attaching a hose for extending the catheter.

The first element of the packaging could have a first end portion and a body portion where the first end portion forms the base. To make the first end portion attachable to the surface of an object, the end portion may comprises a fastening element such as an adhesive, a suction cup etc. The suction cup facilitates the aforementioned characteristics of bonding strongly in a direction perpendicular to the surface whereby the medical article can be removed from the packaging in this direction without releasing the packaging from the surface, whereas the suction cup more easily is released by a pull in a non-perpendicular direction. Furthermore, the suction cup is capable of attaching the packaging to a wet and/or smooth surface, e.g. of tiles in a bathroom. An adhesive may, on the contrary, be difficult to bond to such a wet surface and a through hole or similar means for suspending the packaging on a wall requires a protruding hook-like feature in the room.

The body portion may form a sidewall extending between the base and an opening into a first cavity. The first cavity may form up to 100 hundred percent of the compartment, in which case the opening is closed with an essentially flat closure, e.g. in the form of a foil. It may, however, be desirable to provide the second element with a sidewall extending between a second end portion and an opening into a second cavity which also forms part of the compartment. In this way, it may be provided that the medical article extends from the first cavity into the second cavity, and when the first and second elements are separated, it becomes easy for the user to grab the article by hands or by other suitable means. For this purpose, it may be desirable to provide the packaging so that, when the first and second elements are joined in a closed configuration of the packaging, the first and second end portions form axially opposite end portions of the packaging. A sidewall constituted by the sidewalls of each element may thus have an elongated shape and may extend between the end portions to form an elongated, axially extending, and e.g. straight, compartment for storage of a catheter in a stretched out configuration. The elements could have a tubular wall, e.g. with a circular cross-sectional shape.

The catheter could be of any kind, e.g. of the kind provided with a hydrophilic coating which is activated by a swelling medium, e.g. a saline solution, or the catheter could be provided with a liquid lubricant or a gel. The packaging according to the invention may support such a coating by containing a sufficient amount of the swelling medium or lubricant, or by being essentially impermeable towards the swelling medium or lubricant to allow storage of the catheter even for several years. A more compact packaging and a more homogenous wetting can be achieved by a compartment which narrowly encloses at least the insertable part of the catheter. The packaging may e.g. have a volume in the range of 1 to 20 times, e.g. in the range of 1 to 10 times, such as in the range of 1 to 5 times the volume of the insertable part of the catheter.

In order to avoid spillage of liquids from the packaging, e.g. if the packing contains a swelling medium or lubricant, the opening and base may preferably be located relative to each other so that securing of the packaging on a horizontal surface locates the opening facing upwardly. The packaging may e.g. have a sidewall extending from the base towards the opening in an upright orientation away from the surface, e.g. so that the base forms a vertically lowest area of the packaging and so that the opening forms a vertically highest area of the packaging or at least a vertically highest area of the element to which the base belongs.

By an upright orientation is meant that when the base is attached to a horizontal surface, the sidewall of the packaging then extends from the base in an upward direction away from the surface to which the base is attached and towards the opening through which the medical device can be accessed. To avoid torsion around the base, the packaging may e.g. be designed so that the sidewall extends essentially vertically or at least less than 10 degrees from vertically upwardly from a horizontal surface to which the base is attached. This may be provided by a base which forms an attachment surface or abutment plane which is substantially flat and essentially perpendicular to the sidewall. The base may e.g. have a width in the range of 5-10 percent, such as in the size of 10 percent of the longest length of the packaging. By width is e.g. meant a diameter of a circular base.

When the packaging is supported in such a way on an essentially horizontal surface, the compartment could be formed so that liquid substances in the packaging are collected in a lower most part of the packaging near the base. By arranging the catheter with the insertable part in that lower end of the packaging, that insertable part may be kept in a wet condition when the base is attached to a horizontal surface. When the elements are separated, the user can grip an end of the medical device which is opposite the insertable end, and contamination of the insertable part can therefore be avoided.

To enable easy access to a catheter which is located in the compartment, the catheter could be longer than any of the cavities. In that way, the catheter would extend out of one of the cavities, when the first and second elements are separated. Since the catheter is at least partly exposed, the user could grip the exposed part of the catheter and remove it from the packaging.

To attach the packaging to a surface of an object, the base may comprise a fastening element which is attached to the base or which forms part of the base. The fastening structure may e.g. comprise an adhesive or sticky surface portion, a double sided adhesive label, a surface portion with a structure of the kind known from Velcro™, or a suction cup etc. The suction cup could have a circular flexible rim forming a suction sealing-ring which abuts the surface and deflects. The sealing-ring forms an abutment plane which could be transverse or even perpendicular to the oblong shape of the packaging. When the suction cup is attached to a horizontal surface, the walls of the elements thereby extend transversely or perpendicularly from that surface and form an upright orientation of the packaging in which the opening is above the surface and thus remote from the surface. In another embodiment, the abutment plane is essentially parallel to the oblong shape of the packaging. When this suction cup is attached to a horizontal surface, the walls of the elements extend essentially horizontally and form a horizontal orientation of the packaging. In the horizontal orientation, the packaging could be fixed to an edge portion of a table so that the packaging projects horizontally outward from the surface and the opening thereby becomes essentially in level with the surface but remote therefrom.

"Sterile storage" means that the compartment should facilitate a micro-environment made essentially free of infectious microorganisms at least to a degree which satisfies the intended use of the medical article. To obtain sterility, a sterile catheter could either be packed under sterile conditions, or a catheter could be sealed within the packaging and subsequently be sterilised by methods known in the art, e.g. by radiation.

To maintain sterility, or to preserve a required humidity in the packaging, the first element may comprise a sealing member adapted to seal against the second element for closing the compartment hermetically when the elements are joined. A suction cup and a sealing member both have the characteristics of being relatively easily elastically deformed. The sealing member could advantageously be formed in one piece with the suction cup in a flexible, soft material which is suitable for a suction cup and a sealing member. A remaining part of the first element may be made from a material which is relatively hard compared to the soft material. The first element could e.g. be made in a 2K injection moulding in which both the soft and the hard material is injected in a liquid state into a mould and solidified therein.

The packaging may have a shape which facilitates gripping, in particular for a user suffering from reduced dexterity. The first and optionally the second element of the packaging may therefore be shaped to facilitate gripping thereof, e.g. with a gripping feature—e.g. high frictional surface texture and/or with knobs, protrusions, ribs or depressions which improve handling, or even further by the provision of an outer surface in which a handgrip can fixate the packaging. Since the aforementioned flexible or soft material which forms the suction cup and optionally the sealing member typically provides a good grip when provided on an outer surface of an object, the gripping feature on an outer surface of the first element could be made in one piece with one or both of the suction cup and sealing member. The one piece could e.g. be made in a moulding process, wherein a first material, forming the one piece, are injected into a mould and hardened or solidified therein. Another material which forms the remaining portion of the first element could be moulded in the same mould, e.g. by proceeding, simultaneous or subsequent injection of another material into the same mould and by hardening or solidification of the two different materials in the mould. The other material may e.g. be less elastically deformable than the material forming the suction cup, sealing member and/or the gripping feature.

The first and second elements may be joined by a threaded joint, i.e. one of the parts being provided with an internal threading and the other part having a corresponding outer threading. In this case, an opening procedure may comprise the step of attaching the base to a surface, gripping the part which does not comprise the base and rotating this part, while the base is fixed to the surface.

It may be desired to keep the two elements together after opening of the packaging, or it may be desired to utilise the fastening means on the base to hold both elements to the surface after opening of the packaging. Accordingly, it may be provided for the first element to be selectively attachable at two different locations of the second element. In one of the locations, the compartment is closed, and in the other location, the base of the first element could e.g. be located axially opposite the opening into the second cavity so that the first and second elements extend away from a surface to which the base is attached. For this purpose, the second element may comprise two threaded portions for fixation of a corresponding threaded portion provided on the first element at the two different locations. As an example, the second element could be externally threaded, and the first element could be internally threaded.

In one embodiment, the second end portion of the second element comprises a threaded outer surface for fixation of the first element to form a configuration wherein the first element extends coaxially from the second end portion of the second element. In this configuration, the opening into the second cavity and the base can form axially opposite end portions of the packaging allowing a largest possible distance between the opening into the second cavity and a surface to which the base is attached. In an alternative embodiment, the base is located between the axially opposite end portions to allow attachment of the packaging e.g. In an upright or substantially horizontal orientation.

The first and second elements could be joined in a threaded screw joint, by a releasable sealing strip, by an adhesive, by frictional resistance between the parts, or by any kind of engagement between the two elements.

At least one of the first and second elements could be made from any combination of at least two different materials.

The suction cup, and optionally the sealing member and friction gripping features on an outer surface, could be made from a first material which:
is more resilient than the other material,
could have a more adhesive characteristic than the other material,
could have a different colour than the other materials, or
a combination between the above-mentioned three features.

By resilient is meant that it is more easily deformable, e.g. that it is more easily elastically deformable. The less resilient material may e.g. be a hard plastic material whereas the resilient material could be flexible like a rubber band or like a suction cup.

The first material could be selected from, or contain a mix of materials selected from the group consisting of:
TPE (thermoplastic elastomers), e.g. TPV (V=vulcanisate) such as Santoprene™, styrene bloc copolymer (Kraton™) covering SEBS (Styrene Ethylene Butadiene Styrene), SBS (Styrene Ethylene Styrene) and others, TPU, TPO, COPE (copolyesters), COPA (copolyamides), Synthetic or natural rubber such as Neoprene and latex, or silicone.

As an example, Santoprene™ with hardness in the range of 50-80 shore A could be used as the first material, and the other material could have a different hardness—it could e.g. be harder.

The remaining part of the first and second elements could be made from PP, PE, TPU, Kraton™ or metals such as aluminum etc.

In one embodiment, the second element comprises a base forming a support plane for support of the packaging on a surface of an object, and a sidewall extending from the base in a direction transverse to the support plane towards an upper peripheral edge surrounding the second opening. Corresponding to the first element, the second element may comprise means for securing the element to the surface, e.g. a suction cup or the like. This allows the user to select which part of the packaging it is desired to attach to the object during use of the packaging. Such a suction cup may e.g. form part of the second end portion of the second element or may form part of the sidewall, e.g. moulded in one piece therewith.

In a second aspect, the invention provides a method of removing a medical article such as a catheter from a packaging of the previously described kind. The method comprises:
a) separating the first and second elements while leaving the medical article in the second cavity,
b) attaching the base of the first element to a surface of an object,
c) attaching the second end portion of the second element to the first element, and
d) removing the medical article from the second cavity.

These steps may be carried out in any suitable order, e.g.:

step a) before step b),
step b) before step c)
step c) before step d)
or
step b) before step a),
step a) before step c)
step c) before step d).
or
step a) before step c),
step c) before step b)
step b) before step d).

In a third aspect, the invention provides a method of inserting into a urinary canal, a urinary catheter which is delivered in a packaging of the previously described kind. The method comprises:
   a) separating the first and second elements leaving the catheter in the second cavity,
   b) attaching the base of the first element to a surface of an object,
   c) attaching the second end portion of the second element to the first element
   d) washing hands and an area around the debouchment of the urinary canal,
   e) removing the catheter from the second cavity, and
   f) inserting the catheter into the urinary canal.

The steps a), b), and c) may be conducted in any order, e.g. step a) before step b) before step c), or step b) before step a) before step c).

The method may further comprise steps for enclosing the catheter in the packaging again after the catheter has been used:
   g) arranging the catheter in the second cavity,
   h) detaching the first element from the surface, and
   i) attaching the first element to the second element.

This provides a closed packaging for safe disposal of the urinary catheter.

Step g) should naturally be before step i) but step h) could be before step g), between step g) and step i) or after step i).

DETAILED DESCRIPTION

Figure 2:
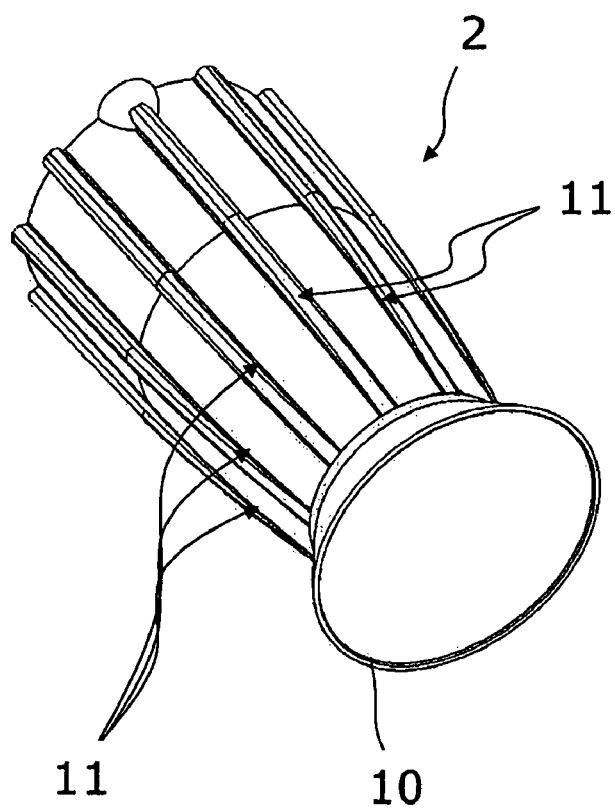
Figure 3:
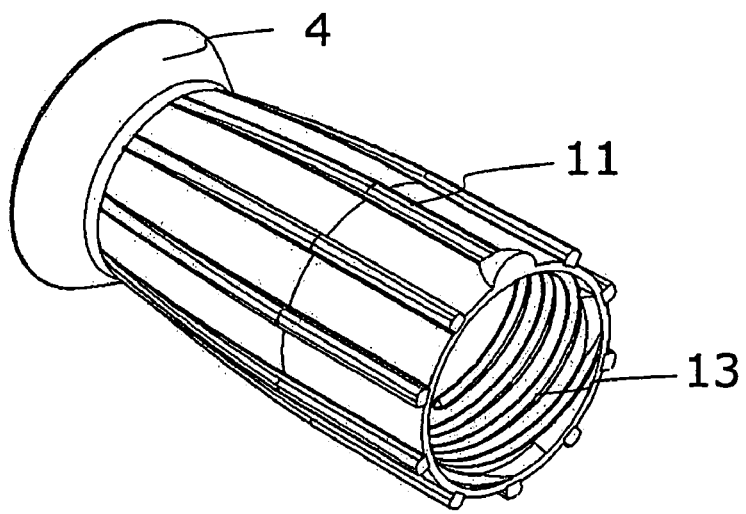
Figure 4:
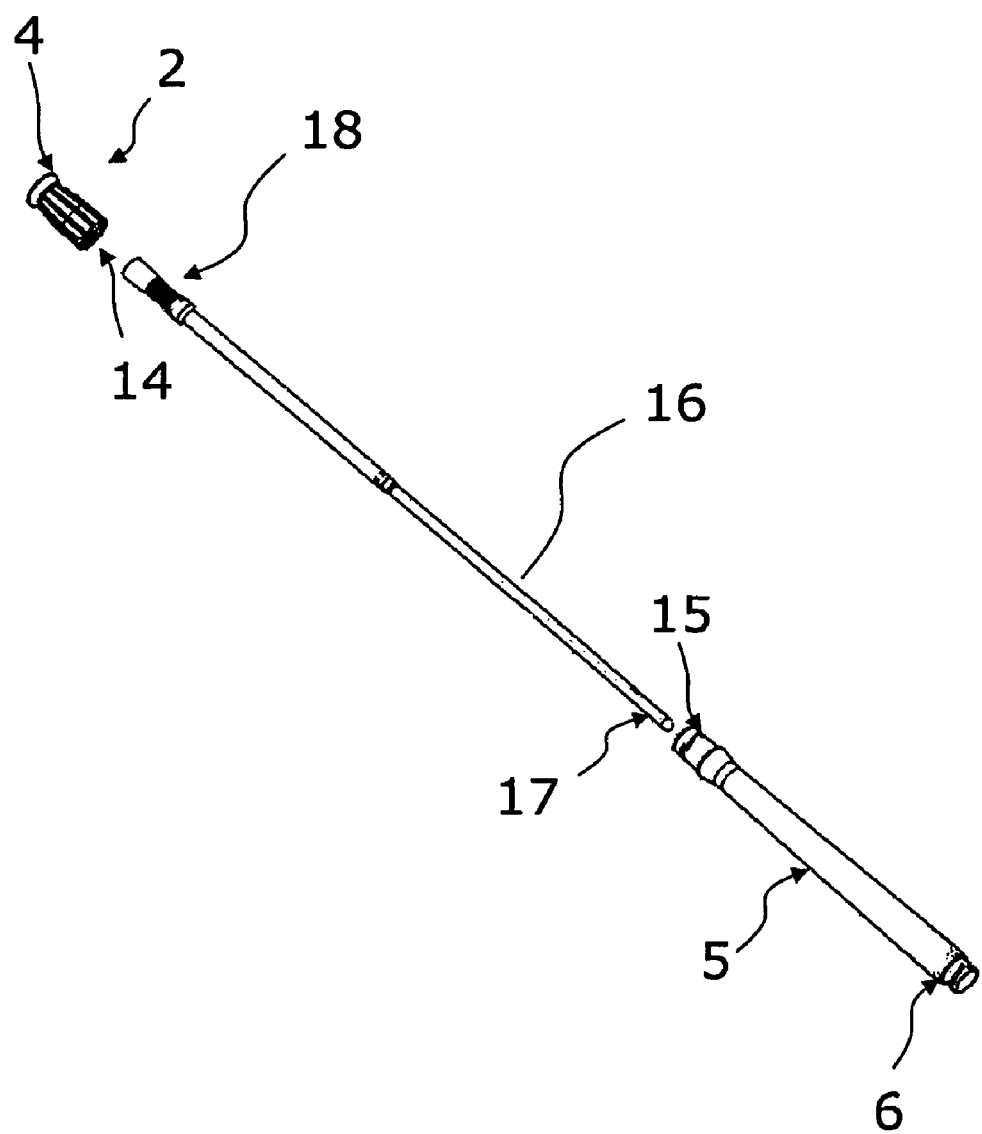
Figure 5:
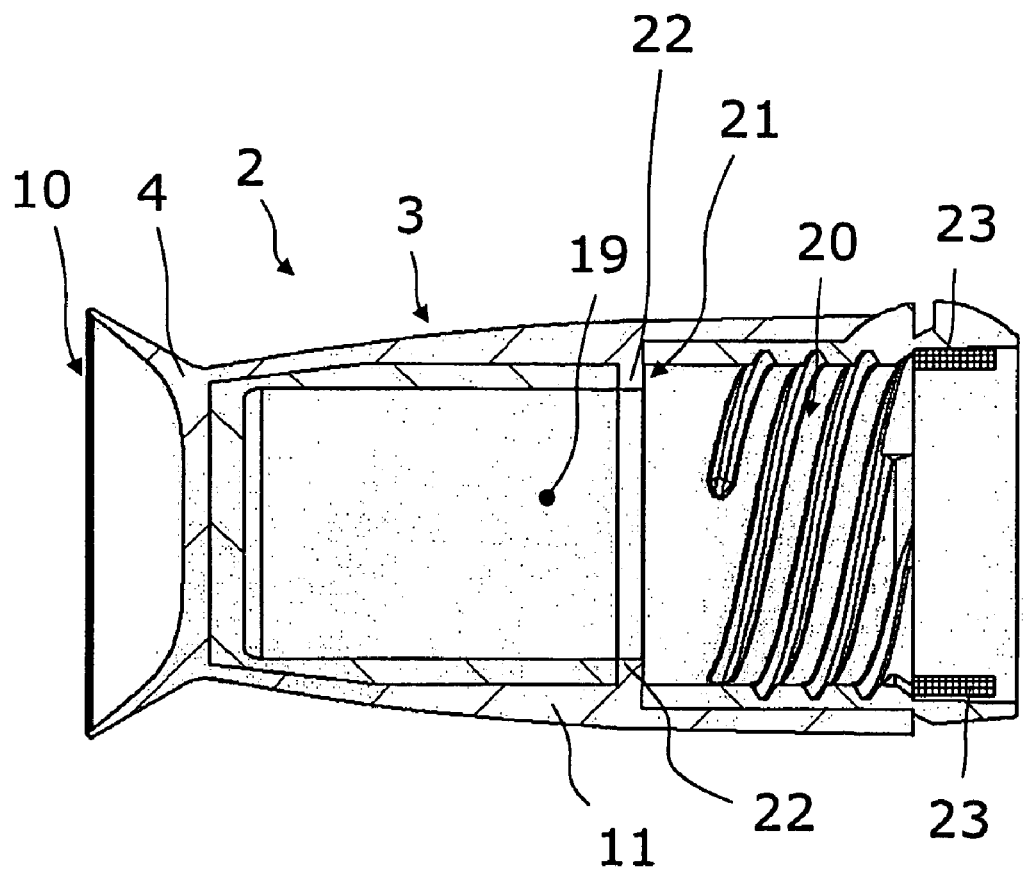

In the following, a preferred embodiment of the invention will be described in further details with reference to the drawing in which:
   FIG. 1 illustrates a packaging 1 for a urinary catheter,
   FIGS. 2 and 3 illustrate a first element with a suction cup,
   FIG. 4 illustrates a packaging during removal of a catheter therefrom, and
   FIG. 5 illustrates a cross-sectional view of the first element.

FIG. 1 illustrates a packaging 1 for a urinary catheter. The packaging comprises a first hollow element 2 comprising a body portion 3 and a base 4. The base is attachable to a surface of an object. The packaging further comprises a second hollow element 5 with a closed second end portion 6. The second end portion could be made from a material which is different from the remaining part of the second element, e.g. a material with a different rigidity, softness, colour etc. The second end portion could be provided as a separate component which is fixed to the remaining portion, or the second hollow element could be formed in one piece.

An opening which provides access to the catheter can be formed by separation of the first element from the second element.

The base 4 forms a suction cup with a suction ring sealing 10 defining a suction face being essentially perpendicular to the axially extending elongated packaging shape which is indicated by the axis 7. When the packaging is attached to a surface of an object, e.g. to a table, a sink or a bathtub, the packaging is upright from that surface and thereby provides a distance from the opening to the surface. This reduces the risk of contamination during removal of the catheter from the packaging.

The proximal end 8 of the body part 3 of the first element 2 is narrow compared to the distal end 9 of the body part 3. The base 4 widens out and defines a flexible suction ring-sealing 10 which defines the suction face. The radial size, i.e. perpendicular to the axial direction (indicated by the axis 7), of the suction ring-sealing 10 is in the size of the radial size of the distal end 9 of the body part 3. The first element comprises a plurality of ribs 11 made in one piece with the suction cup. The second end portion 6 comprises an external threading 12.

FIGS. 2 and 3 illustrate the first element from two directions. The first element comprises an internal threading 13 for joining the first element to the second element, e.g. to close the opening or to arrange the base farthest away from the opening into the second cavity, i.e. with the internal threading 13 engaging the external threading 12. An outer surface of the first element is provided with a gripping feature 11 formed in one piece with the base 4 and thus in one piece with the suction cup.

FIG. 4 illustrates the packaging in an open state wherein the first and second elements 2, 5 are separated to form openings 14, 15 into the cavities. The catheter 16, which is removed from the compartment, has a proximal end 17 for insertion into a urinary canal and an axially opposite distal end 18 provided with a connector for drainage of fluids or for gripping purpose. In the packaging, the catheter is located with the proximal end 17 towards the closed second end portion 6. In the Illustrated embodiment, the catheter comprises telescopic elements and can assume configurations of different length.

FIG. 5 illustrates a cross-sectional view of the first element 2. The element forms a cavity 19 with an internally threaded portion 20 for cooperation with an externally threaded portion of the second element. In this view, the equal radial dimensions of the distal end 8 and the ring-sealing 10 are more clearly seen. The abutment surface 21 comes in contact with the peripheral edge around the opening into the second cavity and thus forms part of a sealing member 22 for establishing a tight connection between the first and second elements and thus a tight encapsulation of the catheter in the compartment. The sealing member 22 is formed in one piece with the base 4 and in one piece with the gripping feature 11. The sealing member 23 is optional and provides an additional or alternative sealing connection with the second element.

The invention claimed is:

1. A packaging with a compartment containing a medical article, the packaging comprising:
   a first element having a first end that is openable for access into the compartment and an second end that is closed;
   a second element that is separable from the first element, the second element having a distal end and a proximal end opposite the distal end, the distal end of the second element is attachable to the closed second end of the first element, and the proximal end of the second element includes a suction cup; and
   a catheter that is insertable into the first element and separable from the first elements and the second element.

2. A packaging according to claim 1, wherein the first and second elements are hollow tubular elements.

3. A packaging according to claim 1, wherein the catheter is longer than the first element and the second element.

4. A packaging according to claim 1, wherein one of the first and second elements comprises a gripping feature on an outer surface of one of the elements.

5. A packaging according to claim 1, wherein attachment of the distal end of the second element to the first end of the first element seals the compartment.

6. A packaging according to claim 1, wherein the distal end of the second element comprises threaded portions for fixation with a corresponding threaded portion on the closed second end of the first element.

7. A packaging according to claim 1, wherein the compartment is formed by the first and second elements and the catheter is fully contained therein.

* * * * *